(12) United States Patent
Münnich et al.

(10) Patent No.: US 8,507,732 B2
(45) Date of Patent: Aug. 13, 2013

(54) PURIFICATION OF TRIS-HYDROXYARYL COMPOUNDS

(75) Inventors: Christian Münnich, Leverkusen (DE); Stephan Konrad, Dormagen (DE); Karl-Heinz Köhler, Aachen-Brand (DE)

(73) Assignee: Bayer Intellectual Property GmbH, Monheim (DE)

( * ) Notice: Subject to any disclaimer, the term of this patent is extended or adjusted under 35 U.S.C. 154(b) by 279 days.

(21) Appl. No.: 13/081,811

(22) Filed: Apr. 7, 2011

(65) Prior Publication Data

US 2011/0251438 A1    Oct. 13, 2011

(30) Foreign Application Priority Data

Apr. 7, 2010  (EP) .................................... 10159247

(51) Int. Cl.
*C07C 39/16*    (2006.01)
*C07C 37/82*    (2006.01)

(52) U.S. Cl.
USPC ........... 568/720; 568/749; 568/753; 568/756; 568/758

(58) Field of Classification Search
USPC ........................................................ 568/720
See application file for complete search history.

(56) References Cited

U.S. PATENT DOCUMENTS

| | | | |
|---|---|---|---|
| 3,037,052 A | | 5/1962 | Bortnick |
| 4,051,079 A | | 9/1977 | Melby |
| 4,191,843 A | | 3/1980 | Kwantes et al. |
| 4,443,635 A | | 4/1984 | McLaughlin |
| 4,992,598 A | * | 2/1991 | Strutz et al. ............... 568/720 |
| 5,012,016 A | * | 4/1991 | Li ............................. 568/720 |
| 5,191,128 A | * | 3/1993 | Li ............................. 568/720 |
| 5,202,505 A | * | 4/1993 | Murphy et al. ............. 568/756 |
| 5,672,776 A | * | 9/1997 | McCloskey et al. ......... 568/756 |
| 5,756,859 A | * | 5/1998 | McCloskey et al. ......... 568/720 |
| 5,763,686 A | * | 6/1998 | McCloskey et al. ......... 568/720 |
| 7,304,189 B2 | * | 12/2007 | Dhalla et al. ............... 568/720 |
| 2006/0173222 A1 | * | 8/2006 | Dhalla et al. ............... 568/720 |

FOREIGN PATENT DOCUMENTS

| | | |
|---|---|---|
| DE | 272786 A1 | 12/1977 |
| EP | 324080 A1 | 7/1989 |
| EP | 441648 A1 | 8/1991 |
| EP | 646613 A2 | 4/1995 |
| EP | 765852 A1 | 4/1997 |
| EP | 782978 A1 | 7/1997 |
| EP | 832868 A2 | 4/1998 |
| EP | 847975 A1 | 6/1998 |
| EP | 930289 A1 | 7/1999 |
| EP | 1369446 A1 | 12/2003 |
| EP | 1458786 B1 | 9/2004 |
| EP | 1500671 A1 | 1/2005 |
| JP | 56-068634 A | 6/1981 |
| JP | 58-105928 A | 6/1983 |
| JP | 2001-114717 A | 4/2001 |

\* cited by examiner

*Primary Examiner* — Brian J Davis
(74) *Attorney, Agent, or Firm* — Novak Druce Connolly Bove +Quigg

(57) ABSTRACT

The present invention is directed to a composition comprising a tris-hydroxyaryl compound having a metal ion impurity content of less than 10 ppm and to a process for the purification of tris-hydroxyaryl compound having a metal ion impurity, comprising at least the following steps:
 a) conditioning a sulphonic acid group-containing active ion exchanger with a solvent which is suitable for the handling of the tris-hydroxyaryl compounds,
 b) producing a solution of the tris-hydroxyaryl compounds to be purified in a solvent which is suitable for the handling of the tris-hydroxyaryl compounds,
 c) contacting the tris-hydroxyaryl compound-containing solution from b) with the conditioned ion exchanger from a),
 d) separating the tris-hydroxyaryl compound-containing solution from c) from the conditioned ion exchanger,
 e) removing at least part of the solvent from the solution of the tris-hydroxyaryl compound separated in d) under low temperature stress.

21 Claims, No Drawings

PURIFICATION OF TRIS-HYDROXYARYL COMPOUNDS

CROSS REFERENCE TO RELATED APPLICATIONS

This application claims benefit to European Patent Application No. 10 159 247.5, filed Apr. 7, 2010, which is incorporated herein by reference in its entirety for all useful purposes.

BACKGROUND OF THE INVENTION

A subject of the invention is tris-hydroxyaryl compounds, preferably 1,1,1-tris(4-hydroxy-phenyl)ethane (THPE), with a content of metal ions, in particular sodium ions, of less than 5 ppm, preferably less than 1 ppm. A further subject of the invention is a process for the production of tris-hydroxyaryl compounds, preferably 1,1,1-tris(4-hydroxyphenyl)ethane (THPE), with a content of metal ions, in particular sodium ions, of less than 5 ppm, preferably less than 1 ppm, by purification of the aromatic hydroxy compounds on acid cation exchange resins.

Tris-hydroxyaryl compounds, in particular THPE, are suitable for the production of branched polycarbonates both by the known phase boundary process and also by the transesterification process with organic carbonates in the melt, so-called polycarbonate melt processes. The use of THPE for the production of branched melt polycarbonate is for example described in EP 1 458 786 A1. In contrast to the phase boundary process, the polycarbonate melt process sets higher requirements for the purity of the starting materials, since undesired by-products cannot be eliminated by a phase separation, but, in particular when they are heavy or non-volatile, such as for example metal salts, remain in the polymer melt and thus lead to undesired side-reactions. this also applies for tris-hydroxyaryl compounds which are used as branching agents in the production of branched melt polycarbonate and are commercially available products. Even traces of metal salts in the lower ppm range, which can be contained as by-products or impurities in such branching agents, have adverse effects on the catalysis of the melt polycarbonate process and lead, as is generally known, to a melt polycarbonate with a markedly increased content of rearrangement products, which for example arise through the so-called Fries rearrangement (A).

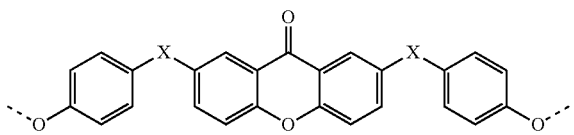

(A)

with X=isopropylidene residue.

The nature and quantity of these defective structures is dependent on various process parameters such as for example temperature, residence time and also above all the nature and quantity of the catalyst used. It is further known that alkali and alkaline earth metal compounds favour the formation of defective structures (e.g. see EP 1 369 446 A1 and EP 1 500 671 A1). Such defective structures are undesired in the melt polycarbonate, since they adversely affect the natural colour of the product and the polymer melt flowability.

Since some of the commercially available tris-hydroxyaryl compounds, such as for example THPE, contain residual contents of metal ions such as for example sodium ions of more than 5 ppm, there was thus a need for tris-hydroxyaryl compounds which are largely free from metallic by-products and an industrially usable process for the purification of tris-hydroxyaryl compounds.

The production of tris-hydroxyaryl compounds, in particular the production of THPE, is known from the literature and for example described in EP 782 978 A1, EP 765 852 A1, EP 930 289 A1, EP 847 975 A1 or EP 441 648 A1. Thus EP 765 852 A1 discloses the synthesis of THPE with the use of ion exchangers and cocatalysts; EP 930 289 A1 discloses the same synthesis with the use of mineral acids. The synthesis of the tris-hydroxyaryl compounds is effected with a large excess of one of the educts, in particular the hydroxyaryl, in order to shift the equilibrium in the direction of the tris-hydroxyaryl compounds. Although the end products in particular according to EP 765 852 A1 should be free from metal ions, residual contents of sodium over 5 ppm are found in the commercial products. Possible causes of these metallic impurities are subsequent treatments of the crude products of THPE with sodium borohydride, as for example described in EP 782 978 A1, or the use of sodium-containing cocatalysts, such as for example sodium mercaptopropanesulphonate, as disclosed in EP 847 975 A1. The addition of sodium-containing stabilisers such as for example sodium dithionite, e.g. disclosed in EP 441 648 A1, can also cause increased sodium contents in commercial THPE. A reduction in the content of other by-products, such as for example sulphur compounds, in the THPE by a subsequent treatment of the THPE with sodium hydroxide solution, see EP 646 613 A1 on this, can also cause increased sodium contents in the THPE end product.

None of the above references describes a process, which leads to a tris-hydroxyaryl end product which is largely free from metallic impurities and is suitable for the production of branched polycarbonate by the melt process wherein the formation of undesired defective structures (Fries structures, xanthone structures) is as far as possible avoided.

There was thus a need for a process with high yield, whereby commercial tris-hydroxyaryl compounds are as far as possible freed of contained metal cations.

The purpose of the invention was thus to provide tris-hydroxyaryl compounds, in particular THPE, with residual metal ion contents of less than 10 ppm, preferably less than 5 ppm in particular from 0.01 to 5 ppm, which overcome the disadvantages of the aforesaid production processes. A further purpose of the invention was to attain residual contents of sodium ions below 5 ppm, preferably less than 1 ppm, in particular from 0.005 to 1 ppm.

Surprisingly, this purpose according to the invention was solved in that commercially available, metal-containing tris-hydroxyaryl compounds are treated under precisely defined conditions with acid cation exchangers, without appreciable observation of the cleavage of the tris-hydroxyaryl compounds back to the starting materials to be expected during this. In particular the expected acid-catalysed removal of phenol and formation of by-products could not be appreciably seen. The tris-hydroxyaryl compounds thus purified are obtained in yields of more than 95% with this process according to the invention and have metal ion contents of less than 5 ppm, preferably less than 1 ppm. On use as branching agents in the melt polycarbonate process, they cause no undesired side-reactions or colour changes.

BRIEF DESCRIPTION OF THE INVENTION

An embodiment of the present invention is a composition comprising a tris-hydroxyaryl compound having a metal ion impurity content of less than 10 ppm.

Another embodiment of the present invention is the above compound, wherein the metal ion impurity comprises sodium ions and wherein the content of sodium ions is less than 5 ppm.

Another embodiment of the present invention is the above compound, wherein the metal ion impurity comprises sodium ions and wherein the content of sodium ions is less than 1 ppm.

Yet another embodiment of the present invention is a process for the production of the above tris-hydroxyaryl compounds, which comprises contacting a solution of one or more tris-hydroxyaryl compounds containing metal ion impurities with one or more acid cation exchangers.

Another embodiment of the present invention is the above process, wherein the contacting of the tris-hydroxyaryl compounds in solution with the ion exchangers is performed at a temperature of −50 to 120° C.

Another embodiment of the present invention is the above process, wherein the contacting of tris-hydroxyaryl compounds with the ion exchangers is carried out batchwise at least once.

Another embodiment of the present invention is the above process, wherein the contacting of tris-hydroxyaryl compounds with the ion exchangers is carried out in a continuous process.

Yet another embodiment of the present invention is a process for the purification of tris-hydroxyaryl compounds having a metal ion impurity, comprising at least the following steps:

a) conditioning a sulphonic acid group-containing active ion exchanger with a solvent which is suitable for the handling of the tris-hydroxyaryl b) producing a solution of the tris-hydroxyaryl compounds to be purified in a solvent which is suitable for the handling of the tris-hydroxyaryl compounds, c) contacting the tris-hydroxyaryl compound-containing solution from b) with the conditioned ion exchanger from a), d) separating the tris-hydroxyaryl compound-containing solution from c) from the conditioned ion exchanger.

Another embodiment of the present invention is the above process, further comprising e. removing a portion of the solvent from the solution of the tris-hydroxyaryl compound separated in d) under low temperature stress.

Another embodiment of the present invention is the above process, further comprising f) precipitating the tris-hydroxyaryl compound in a suitable precipitation agent, and g) gently drying the precipitated tris-hydroxyaryl compound under low temperature stress.

Another embodiment of the present invention is the above process, wherein the removal of the solvents in step e) and/or the drying of the tris-hydroxyaryl compounds in step g) takes place under vacuum.

Another embodiment of the present invention is the above process, which further comprises washing the ion exchanger with water before the conditioning step until the conductivity in an outflow from the column is less than 50 μS/cm, and then washing the ion exchanger with the solvent which is suitable for the handling of the tris-hydroxyaryl compounds, until the water content in a solvent-containing outflow is less than 2 wt. %.

Another embodiment of the present invention is the above process, wherein the ion exchanger is washed with water before the conditioning step until the conductivity in an outflow from the column is less than 20 μS/cm.

Another embodiment of the present invention is the above process, wherein the contacting of the tris-hydroxyaryl compounds in solution with the ion exchangers is performed at temperatures of from −50 to 120° C.

Another embodiment of the present invention is the above process, wherein the contacting of tris-hydroxyaryl compounds with the ion exchangers is carried out batchwise at least once.

Another embodiment of the present invention is the above process, wherein the contacting of tris-hydroxyaryl compounds with the ion exchangers is carried out in a continuous process.

Another embodiment of the present invention is the above process, wherein in step c), a bed of ion exchangers in the form of so-called fixed beds is used.

Another embodiment of the present invention is the above process, wherein the tris-hydroxyaryl compound is 1,1,1-tris(4-hydroxyphenyl)ethane and the solvent is methanol or phenol.

Another embodiment of the present invention is the above process, wherein the acid ion exchangers are based on crosslinked or partially crosslinked polystyrenes.

Another embodiment of the present invention is the above process, wherein the acid ion exchangers are based on crosslinked or partially crosslinked polyacrylates.

Another embodiment of the present invention is the above process, wherein the acid ion exchangers are functionalised with one or more compounds selected from the group consisting of sulphonic acid, carboxylic acid, phosphonic acid, perchloric acid, and mixtures thereof.

DETAILED DESCRIPTION OF THE INVENTION

A subject of the invention is thus a process for the treatment of metal-containing tris-hydroxyaryl compounds, which contains the following process steps:

a) conditioning of a sulphonic acid group-containing active ion exchanger with a solvent which is suitable for the handling of the tris-hydroxyaryl compounds (e.g. methanol or phenol), b) production of a solution of the tris-hydroxyaryl compounds to be purified in a solvent which is suitable for the handling of the tris-hydroxyaryl compounds (e.g. methanol or phenol)

c) continuous or discontinuous contacting of the tris-hydroxyaryl compound-containing solution from b) with a conditioned ion exchanger from a)

d) separation of the tris-hydroxyaryl compound-containing solution from c) from the conditioned ion exchanger, e) if necessary at least partial removal of the solvent from the solution of the tris-hydroxyaryl compound purified in c) under low temperature stress, preferably in vacuo, f) optional, provided that the solvent was not or only partially removed, subsequent precipitation of the tris-hydroxyaryl compound in a suitable precipitation agent and gentle drying under low temperature stress, preferably in vacuo.

Tris-hydroxyaryl compounds to be used according to the invention are e.g.: phloroglucinol, 3,3-bis(3-methyl-4-hydroxyphenyl)-2-oxo-2,3-dihydroindole, 4,6-dimethyl-2,4,6- tris(4-hydroxy-phenyl)-2-heptene, 4,6-dimethyl-2,4,6-tris (4_hydroxyphenyl)-heptane, 1,3,5-tris-(4-hydroxy-phenyl) benzene, 1,1,1-tris(4-hydroxyphenyl)ethane (THPE), tris(4-hydroxyphenyl)phenylmethane, 2,2-bis[4,4-bis(4-hydroxyphenyl)cyclohexyl]propane, 2,4-bis-(4-hydroxyphenylisopropyl)phenol, 2,6-bis(2-hydroxy-5'-methylbenzyl)-4-methylphenol, 2-(4-hydroxyphenyl)-2-(2, 4-dihydroxyphenyl)propane, hexakis(4-(4-hydroxyphenylisopropyl)phenyl)orthoterephthalate, tetrakis (4-hydroxyphenyl)methane, tetrakis(4-(4-hydroxyphenylisopropyl)phenoxy)methane, 1,4-bis((4',4''-dihydroxytri-phenyl)methyl)benzene and isatin biscresol, and optionally also pentaerythritol. The preferred branching agent is THPE.

Ion exchangers usable according to the invention are for example cation exchangers which contain as the polymer matrix a crosslinked or partially crosslinked polystyrene, for example polystyrene crosslinked with divinylbenzene, or a crosslinked or partially crosslinked polyacrylate, for example polyacrylic acid crosslinked with divinylbenzene, with crosslinking levels of 1 to 20%, preferably of 1 to 10%, and which have sulphonic acid groups in the H form (or acid form) chemically bound to the polymer matrix. typical sulphonic acid concentrations of the acid cation exchangers for example 11e in the range from 3 to 7 mol/kg dry weight of the cation exchanger. These ion exchangers can if necessary contain chemically bound further covalently or ionically bound cocatalysts; they are macroporous or in gel form, as described in U.S. Pat. No. 4,191,843 and U.S. Pat. No. 3,037,052 and are in fine particle sphere form, powder form or membrane form.

The acid ion exchanger can be functionalised with one or functions from the group sulphonic acid, carboxylic acid, phosphonic acid and perchloric acid.

One or more ion exchangers can also be used simultaneously or successively by repetition of at least the steps (a) to (d). This has the particular advantage that with the use of several ion exchangers these can be tailored to the ions to be removed at a given time.

In step a), the conditioning of the cation exchangers usable according to the invention should preferably be performed with the same solvent or solvent mixture which is also used for dissolving the tris-hydroxyaryl compounds to be purified. A particularly preferable solvent is methanol or phenol.

The conditioning of ion exchangers comprises two individual steps. In a first step, the ion exchanger is rinsed with water, in order to remove any contained impurities such as traces of acid (washing). In a second step, the purified, water-moist ion exchanger is contacted with a suitable solvent in order to remove the contained water (solvent exchange). Depending on the miscibility of water and the solvent to which the ion exchanger is to be conditioned, a multiple solvent exchange can possibly be necessary. Preferably the conditioning is effected with methanol or phenol. The conditioning to other solvents can be performed analogously.

In the conditioning, in a first step, a sulphonic acid ion exchanger, e.g. Lewatit K1221 (Lanxess AG) is washed electrolyte-free with fully demineralised water, at temperatures from 20° C. to 90° C., preferably from 40° C. to 80° C. If the ion exchanger is washed in a column, the volume flow rate lies in the range from 0.1 to 4, preferably from 0.2 to 2, ion exchanger bed volumes per hour. The ion exchanger is washed electrolyte-free with fully demineralised water until the conductivity in the outflow from the column is preferably less than 50 µS/cm, particularly preferably less than 20 µS/cm. In ion exchanger washing with fully demineralised water performed batchwise, the washing is repeated until conductivity in the aqueous phase after a contact time with the ion exchanger of 1 to 12 hrs, preferably from 2 to 6 hrs, is preferably less than 50 µS/cm, particularly preferably less than 20 µS/cm. The aqueous ion exchanger suspension can be gently stirred during this in order to improve the mass transport, during which the stirring/mixing must be performed so gently that the ion exchanger is not damaged.

Next, the washed ion exchanger can be separated from the liquid aqueous phase e.g. by filtration or decantation.

In a second step the electrolyte-free washed ion exchanger is rinsed with the solvent, preferably methanol or phenol, at temperatures from 0° C. to 60° C., preferably from 20° C. to 50° C., until the water content in the alcoholic outflow is less than 2 wt. %, preferably less than 0.5 wt. %. If the ion exchanger is conditioned in a column, the volume flow rate during this lies held in the range from 0.1 to 4, preferably from 0.2 to 2, ion exchanger bed volumes per hour, until the desired water content in the alcoholic outflow is attained.

Another embodiment of the conditioning is performed batchwise, during which the electrolyte-free washed ion exchanger is contacted with the solvent, preferably methanol or phenol, and the ion exchanger is then separated from the liquid solvent-water mixture, preferably methanol-water mixture or phenol-water mixture. This step is repeated until the solvent-water mixture contains 2 wt. % water, preferably less than 0.5 wt. % water.

The ion exchanger thus conditioned to the solvent, preferably methanol or phenol, can be used for the purification of solutions which contain tris-hydroxyaryl compounds.

In step b), the production of the solutions of the tris-hydroxyaryl compounds to be used according to the invention is preferably effected by dissolution of the tris-hydroxyaryl compounds in distilled solvent at concentrations of 10 g/l to 500 g/l. Suitable solvents are alcohols, in particular methanol, phenol, water or other protic solvents in which the tris-hydroxyaryl compound to be purified has sufficient solubility. Aprotic solvents are also suitable, as long as the tris-hydroxyaryl compounds are sufficiently well dissolved therein and the aprotic solvents do not enter into any side-reactions with the acid ion exchanger, such as for example ether- or ester cleavage. Suitable aprotic solvents are e.g. acetonitrile, dimethyl sulphoxide or chlorobenzene. A mixture of several solvents can also be used.

Solvents which can be removed from the tris-hydroxyaryl compound without subjecting this to exceptional thermal stress are preferable.

The treatment in step c) of the solutions of the tris-hydroxyaryl compounds to be used according to the invention with the ion exchangers usable according to the invention is effected by contacting the tris-hydroxyaryl compound-containing solution with the ion exchanger. The contacting can be performed both continuously and also discontinuously in suitable apparatus. Suitable apparatus for continuously or discontinuously performed processes such as for example columns or stirred vessels are known to those skilled in the art.

Thus for example the tris-hydroxyaryl compound-containing solution can be brought into contact with the ion exchanger in a stirred vessel or mixers of a common type such as for example eccentric tumbler mixers at temperatures from −50° C. to 150° C., preferably from −10° C. to 120° C., particularly preferably from 10° C. to 90° C., for residence times of 0.1 hrs to 6 hrs, preferably from 0.25 hrs to 4 hrs.

In a preferred embodiment of the process according to the invention, the solution containing the tris-hydroxyaryl compound to be purified is passed in step c) through beds of ion exchangers e.g. in the form of so-called fixed beds in suitable temperature-controllable vessels, for example in columns. During this, temperatures from −50° C. to 150° C., preferably −10° C. to 120° C., particularly preferably from 10° C. to 90° C., and residence times from 0.1 hrs to 6 hrs, preferably from 0.25 hrs to 4 hrs, can be used.

In order to obtain the residual ionic metal contents according to the invention in the tris-hydroxy-aryl compounds through the measures a) or b), it can in some cases be necessary to contact the tris-hydroxyaryl compound-containing solution repeatedly with the active cation exchanger.

The ion exchanger can be used several times. Through contacting of the ion exchanger with the tris-hydroxyaryl compound-containing solution, the ion exchanger becomes laden with metal ions which are contained in the solution. As a result, the number of active centres, e.g. sulphonic acid-groups in the protonated form (H form), available for the purification of the tris-hydroxyaryl compound-containing solution falls. If the purifying action of the ion exchanger declines, the ion exchanger can be changed or regenerated. For the regeneration of the metal-laden ion exchanger, the known processes, e.g. rinsing with a proton-containing acid (Brönstedt acid), e.g. dilute hydrochloric acid, and subsequent neutral washing, can be used. Such processes for the regeneration of acid ion exchangers are for example described in EP 324 080 A1, DE-A 2 727 866 or U.S. Pat. No. 4,443,635.

The separation in step d) of the tris-hydroxyaryl compound-containing solution from c) from the conditioned ion exchanger is effected by processes for solid/liquid separation known to those skilled in the art. Such processes are for example filtration or decantation. During these, the solid ion exchanger is separated from the liquid tris-hydroxyaryl compound-containing solution by a suitable solid retaining medium, e.g. a filter.

The solution thus obtained, containing at least one solvent and one tris-hydroxyaryl compound, can optionally be used without further steps. In particular if phenol was used as the solvent, then the solution can be used as such, if necessary after a further purification step, e.g. for the removal of particles.

The at least partial removal of the solvent from the solution of the tris-hydroxyaryl compound purified on the ion exchanger optionally to be performed in step e) should for the avoidance of side-reactions take place under as little thermal stress as possible; preferable temperatures lie in the range from −20° C. to 100° C., preferably from −10° C. to 80° C., particularly preferably from 0° C. to 60° C. Distilling the solvent off in vacuo to reduce the thermal stress is thus preferable.

In step f) the precipitation of the tris-hydroxyaryl compound in a suitable precipitation agent has been found to be particularly gentle. The precipitation can also be effected after prior concentration of the tris-hydroxyaryl compound in the solvent. The precipitated tris-hydroxyaryl compound can be separated from the liquid solution by processes for solid/liquid separation known to those skilled in the art. Such processes are for example filtration or decantation. The solid, solvent-moist tris-hydroxyaryl compound thus obtained is then freed of contained solvent residues by drying.

It has been found advantageous to perform the drying of the purified and precipitated tris-hydroxyaryl compound with low thermal stressing of the tris-hydroxyaryl compound. Preferred temperatures for the drying lie in the range from −20° C. to 100° C., preferably from −10° C. to 80° C., particularly preferably from 0° C. to 60° C. Drying of the purified and precipitated tris-hydroxyaryl compound in vacuo to reduce the thermal stress is preferable.

Through the combination of concentration, subsequent precipitation and gentle drying a particularly high yield of the purified tris-hydroxyaryl compound could be attained.

By treatment of metal ion-containing tris-hydroxyaryl compounds under these conditions according to the invention, cleavage of these compounds on the ion exchangers usable according to the invention could be very efficiently avoided, so that the purified tris-hydroxyaryl compounds can be recovered in very high yield of greater than 95% and in high purity from the purification process according to the invention.

The tris-hydroxyaryl compounds thus purified are particularly suitable for the production of branched melt polycarbonates, since they reduce the formation of Fries rearrangement structures (xanthone structures) as so-called inherent polymer chain branching as a side-reaction in melt polycarbonate production. Hence, with these low metal ion-content tris-hydroxyaryl compounds branched polycarbonates with a low content of Fries structures (xanthone structures) can be produced by the melt polycondensation process. The ratio of branchings to xanthone structures in the polymer chain in the MPC can be efficiently adjusted by means of purified, metal ion-depleted THPE. In this way, melt polycarbonates with a ratio of branching agent structures to xanthone structures in the polymer chain of markedly greater than 10, preferably greater than 15 can be produced.

The purified tris-hydroxyaryl compounds are produced by the melt transesterification reaction of suitable bisphenols and diaryl carbonate esters to polycarbonate in the presence of a suitable catalyst. The polycarbonate can also be produced by the condensation of carbonate oligomers which contain hydroxy and/or carbonate terminal groups and suitable diaryl carbonate esters and bisphenols.

In the context of the present invention, unless otherwise stated, ppb and ppm should be understood to mean parts by weight.

The metal contents can be determined by graphite tube atomic absorption spectrophotometry (graphite AAS) or by ion chromatography (IC) by methods known to those skilled in the art and adequately described in the literature.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

The following examples with 1,1,1-tris(4-hydroxyphenyl) ethane (THPE) as the branching tris-hydroxyaryl compound are intended to illustrate the invention, without limiting it to THPE:

EXAMPLES

Metal Content

The metal content of the samples tested was determined by graphite tube atomic absorption spectrophotometry (graphite AAS).

Compound A

The determination of the concentration of compound A is performed after alkaline hydrolysis of the polycarbonate and subsequent analysis of the hydrolysate by HPLC. The compound was character-ised by nuclear magnetic resonance spectroscopy.

THPE Content

The determination of the concentration of THPE is performed after alkaline hydrolysis of the polycarbonate and subsequent analysis of the hydrolysate by HPLC. The calibration is performed with an external standard.

Purification of Metal Ion-Containing
1,1,1-tris(4-hydroxyphenyl)ethane (THPE)

Example 1

In a glass column, a sulphonic acid ion exchanger (Lewatit K1221, Lanxess AG) is washed electrolyte-free with fully demineralised water at room temperature, during which the volume flow rate is kept constant at 0.3 ml water/ml ion exchanger per hour. After 24 hrs, the conductivity in the outflow from the column is 7 µS/cm. The liquid aqueous phase is discarded and the ion exchanger treated with methanol.

Next, the electrolyte-free washed ion exchanger is rinsed with methanol at room temperature until the water content in the methanolic outflow from the column is less than 0.5 wt. %. During this the volume flow rate is kept constant at 0.3 ml methanol/ml ion exchanger per hour. The ion exchanger thus conditioned to methanol is used for the purification of solutions which contain 1,1,1-tris(4-hydroxyphenyl)ethane (THPE).

A 20 wt. % methanolic THPE solution is passed thus conditioned at room temperature over the ion exchanger. During this, the ion exchanger is contacted with a volume flow of 0.3 ml THPE solution per ml ion exchanger. Next, the ion exchanger is rinsed twice with methanol, during which each time the column volume of the methanol-moist ion exchanger is used as the rinsing volume. The whole column outflow is collected and concentrated under filter pump vacuum at 45° C. until a ca. 50 wt. % solution of THPE in methanol is obtained. This methanolic THPE solution is added at room temperature to double the volume of fully demineralised water. The white precipitate is filtered off and dried for 48 hrs at 50° C. and 48 hrs at 65° C. to constant weight under filter pump vacuum.

Yield: 96.9%
Sodium content of 1,1,1-tris(4-hydroxyphenyl)ethane before purification: 8.3 ppm
Sodium content of 1,1,1-tris(4-hydroxyphenyl)ethane after purification: 610 ppb Example 2

The ion exchanger conditioned in Example 1 is treated at room temperature with a 20 wt. % methanolic 1,1,1-tris(4-hydroxyphenyl)ethane (THPE) solution at a volume flow of 0.3 ml THPE solution per ml ion exchanger. Next, the ion exchanger is rinsed twice with methanol, during which each time 50% of the column volume of the methanol-moist ion exchanger is used as the rinse volume. The whole column outflow is collected and concentrated under the filter pump vacuum at 45° C. until a ca. 50 wt. % solution of THPE in methanol is obtained. This methanolic THPE solution is added with stirring at room temperature to double the volume of fully demineralised water. The white precipitate is filtered off and dried for 24 hrs at 50° C. and 48 hrs at 65° C. to constant weight under filter pump vacuum.

Yield: 97.5%
Sodium content 1,1,1-tris(4-hydroxyphenyl)ethane before purification: 8.3 ppm
Sodium content 1,1,1-tris(4-hydroxyphenyl)ethane after purification: 690 ppb Production of Branched Melt Polycarbonate with Purified and Unpurified 1,1,1-tris(4-hydroxy-phenyl)ethane (THPE)

Examples 3 and 4

Melt polycarbonate (MPC) was produced in a multistage process. Firstly the starting materials BPA, DPC (9000.1 g), tetraphenylphosphonium phenolate (0.7 g) and THPE were melted in a stirred vessel at ca. 190° C. stirred for 45 mins after melting. The quantity of BPA used was selected so that a DPC/BPA ratio on the basis of the substance contents of 110, 108 or 107 mol.-% relative to BPA was established at the start of the reaction. The content of THPE relative to BPA was selected on the basis of the substance contents so that 0.3 mol.-% of THPE relative to BPA were metered in.

For Example 3 not according to the invention, commercially obtainable THPE was used without prior purification. In Example 4 according to the invention, the same commercially obtainable THPE was purified on the acid ion exchanger, as described in Example 1, before use in the MPC reaction.

After a reaction time of 45 min at 190° C. at atmospheric pressure under nitrogen, the reaction mixture is transferred into the sump reservoir of a falling film evaporator. In the falling film evaporator, starting from a temperature of 190° C. a vacuum of ca. 200 mbar is applied and the reaction mixture is pumped in circulation via an externally heated dropping pipe. The circulation pumping volume per unit time is held constant over the experimental period and at the start of the reaction in the falling film evaporator is four times the liquid volume transferred into the falling film evaporator per hour. Phenol forming in the reaction is distilled out, condensed out in a condenser and thus removed from the reaction mixture. After a residence time of 16 mins, the pressure is decreased to 100 mbar and the temperature increased to 220° C. During this, the reaction mixture is pumped in circulation via the dropping pipe. After a residence time of 16 mins, the pressure is reduced to 75 mbar and the temperature increased to 250° C. During this, the reaction mixture is pumped in circulation via the dropping pipe. After a residence time of 16 mins, the pressure is reduced to 50 mbar and the temperature increased to 265° C. During this, the reaction mixture is pumped in circulation via the dropping pipe. After a residence time of 16 mins, the reaction mixture is transferred into a disc reactor. In the disc reactor, the reaction mixture condenses further with rotating discs and a temperature of 270-280° C. and a pressure of 4-6 mbar, during which the phenol formed by the condensation continuously distils off and is thus removed from the reaction mixture. After 45 mins, the pressure is reduced to 0.5-2 mbar and the temperature increased to 300-310° C. The mixture is kept under these reaction conditions until the desired final viscosity is attained. Next, the polymer melt is removed from the disc reactor by means of a gear pump, discharged through a nozzle plate and then granulated after cooling and solidification in a water bath.

Table 1 gives an overview of the experiments with purified and unpurified THPE. Example 3 is not according to the invention, Example 4 is according to the invention.

As Table 1 shows, Example 3 not according to the invention shows a markedly higher content of the structure A of more than 600 mg/kg, in contrast to Example 4 according to the invention, in which the content of the structure A is less than 200 mg/kg. The ratio of THPE to A is markedly lower than ten in the example not according to the invention and markedly greater than ten in the example according to the invention.

TABLE 1

Examples of the production of MPC with different quantities and qualities of THPE.

| Example No. | According to invention | DPC/BPA | Mol. % THPE | Mw, GPC (UV) [g/mol] | THPE in Product [mg/kg] | A in Product [mg/kg] | THPE/A ratio |
|---|---|---|---|---|---|---|---|
| 3 | No | 110 | 0.3 | 33474 | 3500 | 644 | 5.4 |
| 4 | Yes | 107 | 0.3 | 25414 | 3600 | 183 | 19.7 |

In Example 4 according to the invention, the THPE was purified on the ion exchanger before use in the MPC reaction.

Compared to Example 3, the melt polycarbonate prepared with purified THPE in Example 4 has a higher melt viscosity at different shear rates. This is surprising, since the relative viscosity and the content of THPE (branching agent) of Example 3 not according to the invention is comparable with the values of the MPC prepared with THPE purified according to the invention (Example 4). With THPE/A<8, the melt polycarbonate prepared with purified THPE is thus markedly more melt-stable than that in Example 3 not according to the invention.

The invention claimed is:

1. A composition comprising a tris-hydroxyaryl compound having a metal ion impurity content of less than 10 ppm.

2. The composition according to claim 1, wherein the metal ion impurity comprises sodium ions and wherein the content of sodium ions is less than 5 ppm.

3. The composition according to claim 1, wherein the metal ion impurity comprises sodium ions and wherein the content of sodium ions is less than 1 ppm.

4. A process for the production of the composition according to claim 1, which comprises contacting a solution of one or more tris-hydroxyaryl compounds containing metal ion impurities with one or more acid cation exchangers.

5. The process according to claim 4, wherein the contacting of the tris-hydroxyaryl compounds in solution with the ion exchangers is performed at a temperature of −50 to 120° C.

6. The process according to claim 4, wherein the contacting of tris-hydroxyaryl compounds with the ion exchangers is carried out batchwise at least once.

7. The process according to claim 4, wherein the contacting of tris-hydroxyaryl compounds with the ion exchangers is carried out in a continuous process.

8. A process for the purification of tris-hydroxyaryl compounds having a metal ion impurity, comprising at least the following steps:
   a) conditioning a sulphonic acid group-containing active ion exchanger with a solvent which is suitable for the handling of the tris-hydroxyaryl compounds,
   b) producing a solution of the tris-hydroxyaryl compounds to be purified in a solvent which is suitable for the handling of the tris-hydroxyaryl compounds,
   c) contacting the tris-hydroxyaryl compound-containing solution from b) with the conditioned ion exchanger from a),
   d) separating the tris-hydroxyaryl compound-containing solution from c) from the conditioned ion exchanger.

9. The process according to claim 8, further comprising
   e) removing a portion of the solvent from the solution of the tris-hydroxyaryl compound separated in d) under low temperature stress.

10. The process according to claim 9, further comprising
    f) precipitating the tris-hydroxyaryl compound with a suitable precipitation agent, and
    g) drying the precipitated tris-hydroxyaryl compound under low temperature stress.

11. The process according to claim 10, wherein the removal of the solvents in step e) and/or the drying of the tris-hydroxyaryl compounds in step g) takes place under vacuum.

12. The process according to claim 8, which further comprises washing the ion exchanger with water before the conditioning step until the conductivity in an outflow from the column is less than 50 μS/cm, and then washing the ion exchanger with the solvent which is suitable for the handling of the tris-hydroxyaryl compounds, until the water content in a solvent-containing outflow is less than 2 weight %.

13. The process according to claim 11, wherein the ion exchanger is washed with water before the conditioning step until the conductivity in an outflow from the column is less than 20 μS/cm.

14. The process according to claim 8, wherein the contacting of the tris-hydroxyaryl compounds in solution with the ion exchangers is performed at temperatures of from −50 to 120° C.

15. The process according to claim 5, wherein the contacting of tris-hydroxyaryl compounds with the ion exchangers is carried out batchwise at least once.

16. The process according to claim 5, wherein the contacting of tris-hydroxyaryl compounds with the ion exchangers is carried out in a continuous process.

17. The process according to claim 8, wherein in step c), a bed of ion exchangers in the form of fixed beds is used.

18. The process according to claim 8, wherein the tris-hydroxyaryl compound is 1,1,1-tris(4-hydroxyphenyl)ethane and the solvent is methanol or phenol.

19. The process according to claim 5, wherein the acid ion exchangers contain crosslinked or partially crosslinked polystyrenes.

20. The process according to claim 5, wherein the acid ion exchangers contain crosslinked or partially crosslinked polyacrylates.

21. The process according to claim 5, wherein the acid ion exchangers are functionalised with one or more compounds selected from the group consisting of sulphonic acid, carboxylic acid, phosphonic acid, perchloric acid, and mixtures thereof.

* * * * *